(12) United States Patent
Manning

(10) Patent No.: US 6,409,719 B1
(45) Date of Patent: Jun. 25, 2002

(54) LIGHT STINT IMPLANT DEVICE FOR TREATMENT OF LONG TERM VIRAL INFECTION

(76) Inventor: Don A. Manning, 4370 S. Alabama, Monroeville, AL (US) 36460

( * ) Notice: Subject to any disclaimer, the term of this patent is extended or adjusted under 35 U.S.C. 154(b) by 106 days.

(21) Appl. No.: 09/663,786

(22) Filed: Sep. 18, 2000

(51) Int. Cl.[7] .............................................. A61B 18/18
(52) U.S. Cl. .............................. 606/14; 606/7; 606/41; 606/42; 607/88; 607/92; 607/98; 607/94; 607/100; 604/21; 604/288.01; 604/288.02
(58) Field of Search ................................ 606/7, 13, 14, 606/41, 42; 607/92–94, 100; 604/4.01, 6.03, 6.08, 21, 43, 288.01, 288.02, 891.1

(56) References Cited

U.S. PATENT DOCUMENTS

| | | | |
|---|---|---|---|
| 4,960,408 A | 10/1990 | Klainer et al. | |
| 4,979,936 A | * 12/1990 | Stephenson et al. | .......... 600/16 |
| 5,251,622 A | * 10/1993 | Robson | .......... 607/19 |
| 5,524,632 A | * 6/1996 | Stein et al. | .................. 128/733 |
| 5,531,741 A | 7/1996 | Barbacci | |
| 5,895,786 A | 4/1999 | Ben-Hur et al. | |
| 5,902,475 A | 5/1999 | Trozera et al. | |
| 5,964,751 A | 10/1999 | Amplatz et al. | |
| 6,010,890 A | 1/2000 | Ben-Hur et al. | |
| 6,019,784 A | 2/2000 | Hines | |
| 6,090,599 A | 7/2000 | Ben-Hur et al. | |

* cited by examiner

Primary Examiner—Linda C. M. Dvorak
Assistant Examiner—Ahmed Farah
(74) Attorney, Agent, or Firm—Randal D. Homburg

(57) ABSTRACT

A light stint implant device adapted to be surgically implanted in a major blood vessel for assisting in the treatment of long term viral infection, alone or in combination with anti-viral drugs, is disclosed. The implant device is programmed for set periods of illumination and set periods of dormancy through a remote power supply and timing device accessible through a sub-dermal implant adapted to be surgically placed in a location under the skin. The device, after being implanted within such blood vessel will eliminate viruses located within the blood through exposure to light given off by the light stint implant device during the periods of illumination.

4 Claims, 2 Drawing Sheets

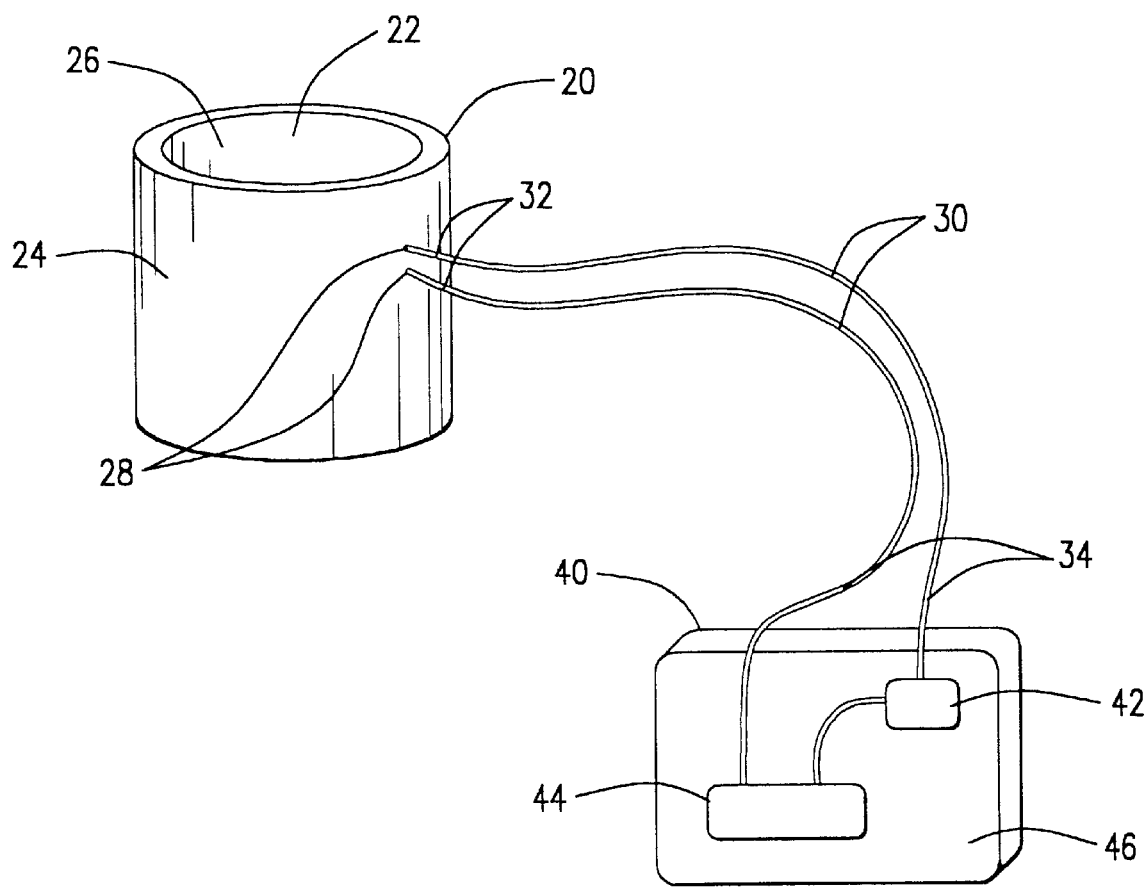
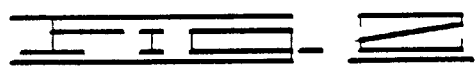

LIGHT STINT IMPLANT DEVICE FOR TREATMENT OF LONG TERM VIRAL INFECTION

CROSS REFERENCE TO RELATED APPLICATIONS

None

BACKGROUND OF THE INVENTION

1. Field of Invention

The invention is a light stint implant surgically implanted in a major artery for assisting in the treatment of long term viral infection, alone or in combination with anti-viral drugs, such implant stint being activated for set periods of illumination and set periods of dormancy, the light stint having a remote power supply and timing device accessible through a sub-dermal implant located in a non-obvious location.

2. Description of Prior Art

The following United States patents were discovered and are disclosed within this application for utility patent. All relate to treatment of viral disease or blood with light, stints or immunology. Three patents dealing with the treatment of viral infection using red light or light and introducing phthalocyanide, a liposome carrier or 5-aminolevulinic acid, such treatment and methods disclosed in U.S. Pat. Nos. 6,090,599, 6,010,890 and 5,895,786 to Ben-Hur, et al. A method including the introduction of psoralen compounds and activation by exposure to UV light to treat the AIDS virus is disclosed in U.S. Pat. No. 4,960,408 to Klainer, such activated chemical compounds attacking the free virus and viral infected cells in patients with depressed immune function.

A method for the manufacturing of a stint is disclosed in U.S. Pat. No. 5,902,475 to Trozera, et al. and 6,019,784 to Hines. An illuminated urethral stint is disclosed in U.S. Pat. No. 5,531,741 to Barbacci which assists in the determination of damage to the urethral structure without more invasive observation technique. A light delivery system with blood flushing characteristics is disclosed in U.S. Pat. No. 5,964,751 to Amplatz, et al., which is provided for percutaneous transluminal coronary angioplasty procedures, the device including an illumination means and means for flushing the illumination and balloon chambers with a saline solution to provided radiant energy to a specific treatment site to reduce the incidence of restenosis.

SUMMARY OF THE INVENTION

The primary objective of the invention is to provide an implanted illuminated stint in a major artery of the human body which, in combination with known anti-viral treatment drug, to improve the effectiveness of T-cells and other natural viral inhibitors in the reduction of the virus and the effect of the viral infection in the human body, especially in those with virus infection which cannot be eliminated through presently know methods of treatment, including the AIDS virus.

Another objective is to provide a UV, infrared or visual spectrum light stint in the descending aorta of the human body, which, in combination with leukine and sargramostim, periodically irradiates the entire human blood supply with such light emitted by the stint and is a permanent surgical implant with permanent cyclic treatment, the power supply to such stint provided by a sub-dermally implanted control unit, having a low-voltage, long life power source and a timing control means to activate and deactivate the illumination of the light stint at pre-determined cycles, such control unit accessible just under the skin of the person having the implanted light stint.

It is known in the medical arts that light, including infrared, visible and ultraviolet, will destroy or severely disable a virus, and several means indicated in the section above include inventions which address this treatment. However, none of them disclose a permanent implant or means which activates a light source within the flow of blood in periodic cycles to weaken and destroy active viruses within the blood, especially in combination with T-cell stimulating drugs which bolster and enhance the effectiveness of the T-cells is the human body is seeking out and destroying viruses. The same light which is effective in destroying the viruses is also a stimulant to T-cell production in the human body, thereby defining such light as both a benefit to positive viral disease treatment while being a negative to the actual viral disease.

DESCRIPTION OF THE DRAWINGS

The following drawings are submitted with this utility patent application.

FIG. 2 is a drawing of the light stint and the control unit.

DESCRIPTION OF THE PREFERRED EMBODIMENT

Figure 1:
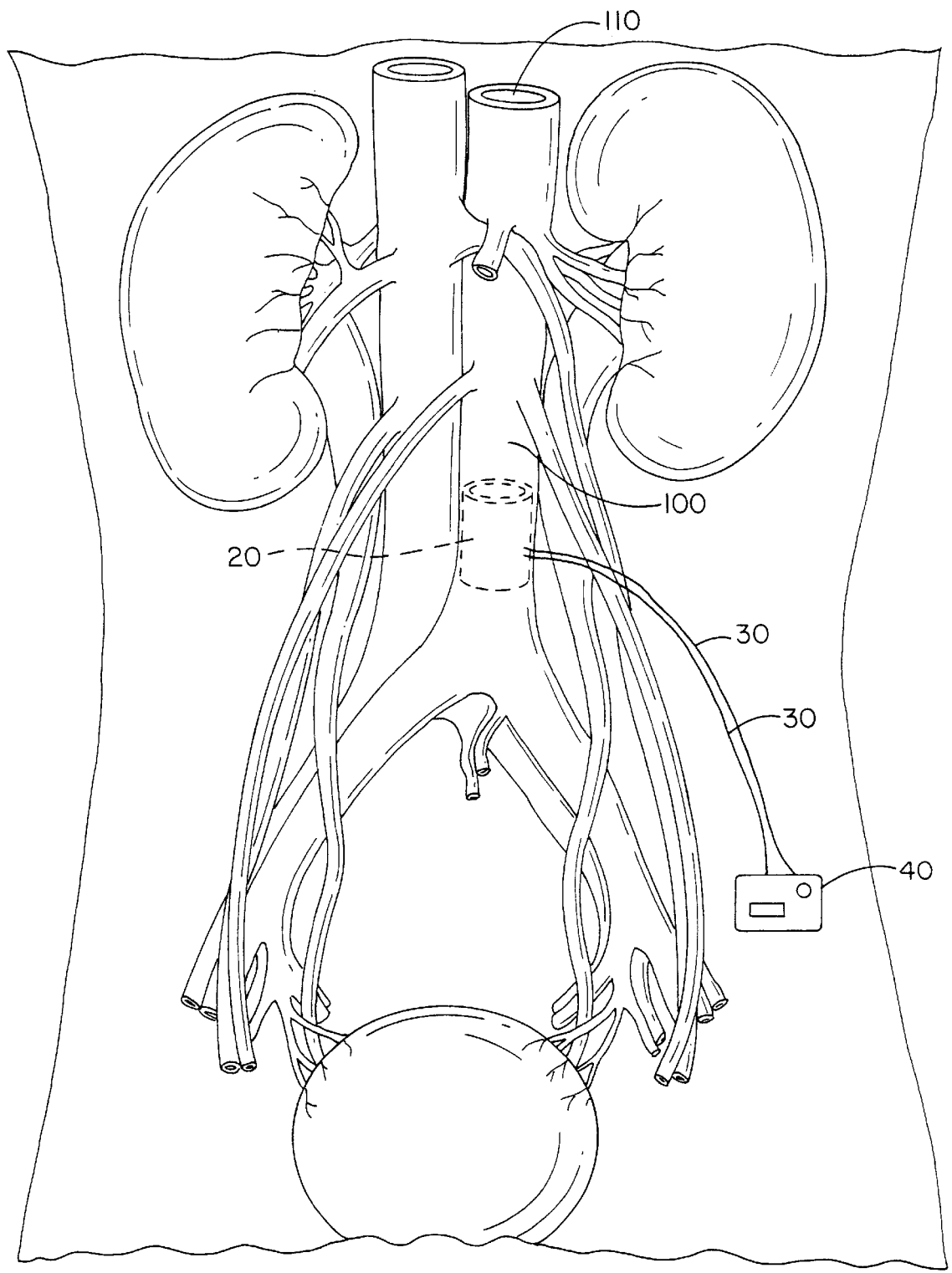
FIG. 1 is a drawing of the light stint in a major artery of the human body.

The invention, as shown in FIGS. 1 and 2 of the drawings, is a thin, illuminating cylindrical light stint device 10 for implant within and against an inner wall 110 of a major artery 100 in a human body, preferably the descending aorta, the invention comprising a thin, hollow, cylindrical illuminating light stint 20, having an inner surface 22 and an outer surface 24, the illuminating light stint 20 being surgically implanted within the chosen main artery 100 of the human body. The illuminating light stint 20 conforms to inner wall 110 of the major artery 100 with the outer surface 24 of the illuminating light stint 20 against the inner wall 110 of the major artery 100, allowing the blood flow through the major artery 100 to pass along the inner surface 22 of the illuminating light stint 20. The illuminating light stint 20 has an illumination means 26 emitting light from the inner surface 22, such illumination means 26 providing light in the ultraviolet, infrared and visible spectrums.

The illuminating light stint 20 has electrodes 28 in its outer surface 24 connecting to a first end 32 of a pair of electronic leads 30, such electronic leads 30 passing through the major artery 100. The pair of electronic leads 30 must pass through the major artery 100 without causing any blood loss through the major artery 100.

A second end 34 oft he pair of electronic leads 30 is connected to an inner low voltage, long-term power supply 42 within an ultra-thin control unit 40. The control unit 40 is also surgically implanted within the human body, but most preferably, is implanted at a sub-dermal location accessible without significant intrusion into the human body. The control unit 40 also contains a programmable timing means 44 which activates and deactivates the inner low voltage, long-term power supply 42 in a pre-set cyclic pattern, programmable at the time the control unit is surgically implanted. The inner low voltage, long-term power supply 42 and the programmable timing means 44 are accessible within the control unit 40 by a removable access panel 46 located on the control panel 40 closest to the skin of the human within which the control unit 40 is implanted.

Once surgically implanted, programmed and connected, the illuminating light stint 20 is illuminated when the programmable timing means 44 activates the inner low voltage, long-term power supply 42, thereby providing light to the inner surface 22 oft he illuminating light stint 20 and illuminating the flowing of blood traveling through the illuminating light stint 20. While the programmable timing means 44 of the control unit 40 is preferably programmed at the time of surgical implant, such programmable timing means 44 may be reprogrammed at any time with minimal invasion or trauma to the person within which the invention is applied, provided the control unit 40 is sub-dermally implanted with the removable access panel 46 just beneath the dermal layer. Likewise, the inner low voltage, long-term power supply 42 may be replaced with the same minimal invasion or trauma by accessing the same removable access panel 46.

The illuminating light stint 20 is preferably activated for a short period of time within a set cycle, being activated for a long enough period for the blood supply for the entire human body to have passed through the illuminating light stint 20 several times during the active cycle. In person having the AIDS virus or other long term viral infections, more frequent illumination cycles would be programed into the control unit to provide more light exposure to the blood. The cycles may also be programmed to correspond to the medically prescribed times of introduction of other medicines being used to treat the viral disease to enhance the effectiveness of the medicines during their maximum concentration within the blood stream.

Reprogramming of the programmable timing means 44 may also be provided by remote using microwave or other efficient waveform transmission. In this remote embodiment, the programmable timing means 44 would require a remote transmission receiver attaching to such programmable timing means 44.

While the invention has been particularly shown and described with reference to a preferred embodiment thereof, it will be understood by those skilled in the art that changes in form and detail may be made therein without departing from the spirit and scope of the invention.

What is claimed is:

1. A light stint implant device adapted to be surgically implanted in a major artery for assisting in the treatment of long term viral infection, alone or in combination with anti-viral drugs, the invention comprising:
    a. a thin, hollow, cylindrical illuminating light stint adapted to be implanted within the major artery having an illuminating means, an inner surface and an outer surface, the outer surface being provided with electrodes;
    b. a pair of electronic leads having a first end and a second end, the first end of the electronic leads connected to the electrodes on the outer surface of the illuminating light stint; and
    c. a control unit containing a removable access panel, an inner low voltage, long-term power supply connected to the second end of the electronic leads and a programmable timing means connected to the inner low voltage, long-term power supply to periodically activate the inner low voltage, long-term power supply causing such inner low voltage, long-term power supply to activate the illuminating means in the illuminating light stint providing light to the inner surface of the illuminating light stint and blood flowing along the inner surface of the illuminating light stint.

2. The invention as disclosed in claim 1, wherein the illuminating means provides light in the infrared, visible and ultraviolet spectrum.

3. The invention, as disclosed in claim 1, wherein the invention is utilized in conjunction with leukine and sargramostim for the treatment of AIDS.

4. The invention as disclosed in claim 1, further comprising the control unit having a remote transmission receiver for remotely reprogramming the programmable timing means, avoiding the need to access such programmable timing means through the removable access panel.

* * * * *